US012723276B2

(12) United States Patent
Wu et al.

(10) Patent No.: US 12,723,276 B2
(45) Date of Patent: Sep. 1, 2026

(54) METHOD TO CALIBRATE NUCLEIC ACID LIBRARY SEEDING EFFICIENCY IN FLOWCELLS

(71) Applicant: Illumina, Inc., San Diego, CA (US)

(72) Inventors: Yir-Shyuan Wu, Albany, CA (US); Filiz Gorpe-Yasar, Redwood City, CA (US); Jeff Fisher, San Diego, CA (US); Jeff Brodin, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 798 days.

(21) Appl. No.: 18/013,788

(22) PCT Filed: Jul. 2, 2021

(86) PCT No.: PCT/US2021/040245
§ 371 (c)(1),
(2) Date: Dec. 29, 2022

(87) PCT Pub. No.: WO2022/006495
PCT Pub. Date: Jan. 6, 2022

(65) Prior Publication Data

US 2023/0242967 A1 Aug. 3, 2023

Related U.S. Application Data

(60) Provisional application No. 63/047,817, filed on Jul. 2, 2020.

(51) Int. Cl.

| | |
|---|---|
| ***C12Q 1/6806*** | (2018.01) |
| ***C12N 15/10*** | (2006.01) |
| ***C12Q 1/6851*** | (2018.01) |
| ***C12Q 1/6876*** | (2018.01) |

(52) U.S. Cl.
CPC ....... *C12Q 1/6806* (2013.01); *C12N 15/1068* (2013.01); *C12Q 1/6851* (2013.01); *C12Q 1/6876* (2013.01); *C12Q 2600/16* (2013.01)

(58) Field of Classification Search
CPC .. C12Q 1/6806; C12Q 1/6851; C12Q 1/6876; C12Q 2600/16; C12Q 2535/122; C12Q 2539/101; C12Q 2545/114; C12Q 2563/159; C12Q 2565/543; C12N 15/1068
See application file for complete search history.

(56) References Cited

U.S. PATENT DOCUMENTS

2019/0153438 A1* 5/2019 Vuyisich ............ C12N 15/1068

FOREIGN PATENT DOCUMENTS

| | | | | |
|---|---|---|---|---|
| JP | 2002516167 | A | 6/2002 | |
| JP | 2014518639 | A | 12/2012 | |
| WO | 9961128 | A1 | 12/1999 | |
| WO | 2012168812 | A1 | 12/2012 | |
| WO | 2015/189621 | A1 | 12/2015 | |
| WO | WO-2015189637 | A1 * | 12/2015 | ........... C12Q 1/6869 |
| WO | 2018/161019 | A1 | 9/2018 | |

OTHER PUBLICATIONS

Illumina, "Optimizing Cluster Density on Illumina Sequencing Systems", pp. 1-12, (Year: 2016).*
Quail et al., "A Large Genome Center's Improvements to the Illumina Sequencing System," Nature Methods, vol. 5, No. 12, pp. 1005-1010, 2008.
Gabriels, Jan, International Search Report & Written Opinion, PCT/US2021/040245, European Patent Office, Oct. 21, 2021.
Chatel, Cecile, International Preliminary Report on Patentability and Written Opinion, PCT/US2021/040245, The International Bureau of WIPO, Jan. 12, 2023.
Brinkman et al., "Whole-genome DNA methylation profiling using MethylCap-seq", Methods, 2010, 5 pages.

* cited by examiner

*Primary Examiner* — Cynthia B Wilder
(74) *Attorney, Agent, or Firm* — Illumina, Inc.

(57) ABSTRACT

The disclosure provides methods to calibrate polynucleotide seeding efficiency in flow cells.

21 Claims, 6 Drawing Sheets

Specification includes a Sequence Listing.

Supernatant from pattern FC
After 5 min incubation at 40C

Supernatant from regular FC
After 5 min incubation at 40C

Supernatant from pattern FC
After 60 min incubation at 40C

Supernatant from regular FC
After 60 min incubation at 40C

METHOD TO CALIBRATE NUCLEIC ACID LIBRARY SEEDING EFFICIENCY IN FLOWCELLS

CROSS REFERENCE TO RELATED APPLICATIONS

This application is a U.S. National Phase Application filed under 35 U.S.C. § 371 and claims priority to International Application No. PCT/US2021/040245, filed Jul. 2, 2021, which application claims priority to U.S. Provisional Application Ser. No. 63/047,817, filed on Jul. 2, 2020, the disclosures of which are incorporated herein by reference.

TECHNICAL FIELD

The disclosure provides methods to calibrate polynucleotide seeding efficiency in flow cells.

BACKGROUND

Flow cells for sequencing are glass slides containing small fluidic channels, through which polymerases, dNTPs and buffers can be cycled. The glass inside the channels is decorated with short oligonucleotides complementary to adapter sequences on target nucleic acids. The target nucleic acids containing adapters are diluted and hybridized to these oligonucleotides, temporarily immobilizing individual DNA strands onto the flow cell ("polynucleotide seeding"). Library strands are then amplified using, e.g., a "bridge-PCR" strategy employing cycles of primer extension followed by chemical denaturation. Through an in-situ amplification process, the strands are amplified by several thousand. Target nucleic acids are hybridized to the flow cell in low molar quantities (6-20 pM). This results in a large physical separation between template DNA strands. At the end of amplification, small clusters of identical DNAs are left as molecules immobilized on a 2D surface, that can be sequenced en masse.

SUMMARY

The efficiency of polynucleotide seeding in flow cells is typically determined by counting the final cluster numbers. The disclosure provides a new and improved method to determine the efficiency of polynucleotide seeding in flow cells.

The disclosure provides a method to evaluate the seeding efficiency of a flow cell with polynucleotides, comprising: seeding a flow cell with polynucleotides for at least 1 minute and (i) contacting the flow cell with a labelled agent that binds to or incorporates onto seeded polynucleotides and determining the amount of label present in the flow cell thereby determining the seeding efficiency; or (ii) collecting the supernatant; quantifying the polynucleotides in the supernatant by using step (a) or (b): (a) amplifying the polynucleotides in the supernatant using qPCR and/or droplet PCR; or (b) reseeding the supernatant using a second flow cell and counting clusters generated after bridge amplification of the polynucleotides; and (c) determining seeding efficiency of the flow cell by comparing the number of polynucleotides quantified in the supernatant vs. the number of polynucleotides used to seed the flow cell. In one embodiment, the labelled agent comprises labelled dNTPs that are incorporated onto a seeded polynucleotide by a polymerase. In another embodiment, the labelled agent comprises a labelled nanoparticle or labelled dendrimer that binds to a complementary oligonucleotide on a seeded polynucleotide. In still another embodiment, the labelled agents comprises a labelled adapter or labeled complementary oligo to a seeded polynucleotide. In yet another embodiment, the labelled agent comprises a labelled structure grown from an end of a seeded polynucleotide. In another or further embodiment, the label is a luminescent or fluorescent detectable label.

In one embodiment, the methods determines seeding efficiency by looking at the polynucleotides that are not captured on the surface and remain in the bulk seeding solution. By collecting and analyzing the supernatant from the flow cell channel at the end of seeding process, more detailed information regarding the seeding process can be determined. The methods disclosed herein are especially useful for checking the seeding on patterned flow cells, in which the cluster number does not directly correlate to number of polynucleotides seeded due to, but not limited to, (1) poly-clonality, (2) ex-amplification duplicates, and (3) library adsorption at interstitial areas between wells.

In a particular embodiment, the disclosure provides a method to evaluate the seeding efficiency of a flow cell with polynucleotides, comprising: seeding a flow cell with polynucleotides for at least 1 minute and collecting the supernatant; quantifying the polynucleotides in the supernatant by using step (a) or (b): wherein (a) comprises amplifying the polynucleotides in the supernatant using qPCR and/or droplet PCR; or (b) comprises reseeding the supernatant using a second flow cell and counting clusters generated after bridge amplification of the polynucleotides; and determining seeding efficiency of the flow cell by comparing the number of polynucleotides quantified in the supernatant vs. the number of polynucleotides used to seed the flow cell. In a further embodiment of any embodiment disclosed herein, one channel of a flow cell is evaluated for polynucleotide seeding efficiency. In a further embodiment of any embodiment disclosed herein, more than one channel of a flow cell is evaluated for polynucleotide seeding efficiency. In a further embodiment of any embodiment disclosed herein, the flow cell comprises a plurality of primers bound to the surface of the flow cell. In a further embodiment of any embodiment disclosed herein, the bound primers comprise P5 primers which have the sequence of SEQ ID NO:1 and/or are P7 primers which have the sequence of SEQ ID NO:2. In a further embodiment of any embodiment disclosed herein, the plurality of primers are randomly bound to the surface of the flow cell. In a further embodiment of any embodiment disclosed herein, the plurality of primers are bound to specific areas of flow cells. In a further embodiment of any embodiment disclosed herein, the plurality of primers are bound to the surface of an array of wells that are patterned on the flow cell surface. In a further embodiment of any embodiment disclosed herein, the flow cell is used in a next generation sequencing device. In a further embodiment of any embodiment disclosed herein, the polynucleotides comprise adaptors. In a further embodiment of any embodiment disclosed herein, the adaptors are bridge PCR compatible. In a further embodiment of any embodiment disclosed herein, the polynucleotides comprise a DNA library. In a further embodiment of any embodiment disclosed herein, the DNA library is generated using a library preparation kit. In a further embodiment of any embodiment disclosed herein, the DNA library is prepared according to a method comprising the steps: (A) simultaneous fragmenting and adding primers to isolated DNA using transposomes; (B) amplifying the fragmented DNA using reduced-cycle PCR, wherein the PCR amplification primers comprise index and adapter sequences; and (C) washing and pooling the amplified DNA fragments to form a DNA library. In another or further embodiment disclosed herein, the transposomes are linked to beads. In another or further embodiment disclosed herein, the DNA library is generated from genomic DNA isolated from a human subject. In another or further embodiment disclosed herein, the polynucleotides are seeded in the flow cell from 5 min to 60 min. In another or further embodiment disclosed herein, the polynucleotides are seeded in the flow cell for 10 min to 40 min. In another or further embodiment disclosed herein, the qPCR comprises using a double stranded binding dye that allows for quantification of a double stranded amplified product based upon the level of fluorescence. Examples of double stranded binding dyes include, but are not limited to, SYBR® Green I, BRYT Green® Dye, PicoGreen, YOYO-1 iodide, and SYBR® Gold. In another or further embodiment disclosed herein, the qPCR comprises a sequence specific probe that is labeled with a fluorescent reporter and a quencher molecule that binds to a DNA template. In another or further embodiment disclosed herein, the quencher molecule is a dark quencher that absorbs light over multiple wavelengths and does not emit light. Examples of dark quenchers include, but are not limited to, Dabsyl, Black Hole Quenchers, Iowa Black FQ, Iowa Black RQ, IRDye QC-1, and Qxl quenchers. In another or further embodiment disclosed herein, the second flow cell used to quantitate the polynucleotides in the supernatant is different from the flow cell that is seeded with polynucleotides. In another or further embodiment disclosed herein, the second flow cell provides up to 12 Gb of sequence data per run while the flow cell that is seeded with polynucleotides provides up to 120 Gb of sequence data per run. In another or further embodiment disclosed herein, the method is performed multiple times using flow cells that were seeded with the same concentration of polynucleotides but with different seeding lengths of time. In another or further embodiment disclosed herein, the seeding efficiency of a flow cell with polynucleotides is evaluated over various time points in time-lapse fashion.

In a certain embodiment, the disclosure provides for the use of a method disclosed herein for the engineering of flow cell surfaces that have improved seeding efficiencies for polynucleotides.

The details of one or more embodiments of the disclosure are set forth in the accompanying drawings and the description below. Other features, objects, and advantages will be apparent from the description and drawings, and from the claims.

Figure 1:
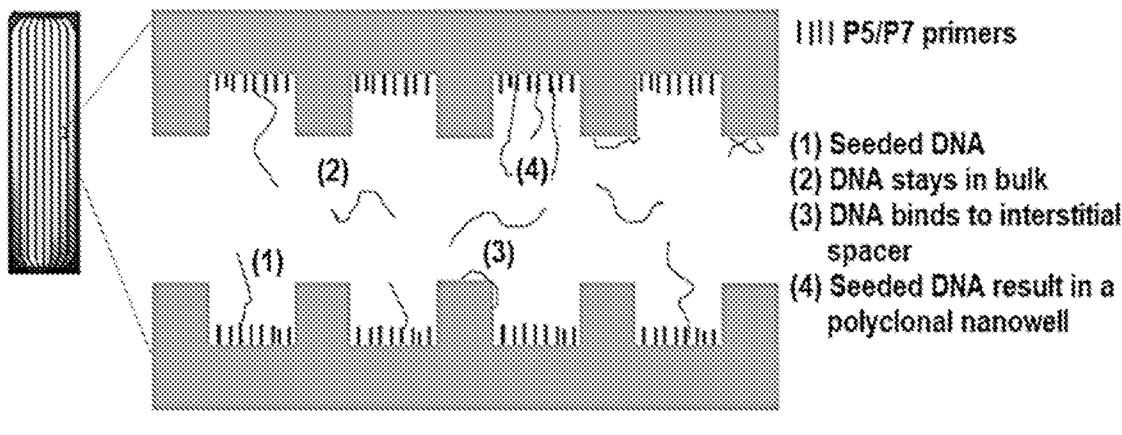
FIG. 1 provides an illustration of DNA seeding process in a patterned flow cell. Due to the multiple destinations of DNA molecules, the most effective way to calibrate the seeding process is to collect supernatant and analyze it.

The accompanying drawings, which are incorporated into and constitute a part of this specification, illustrate one or more embodiments of the disclosure and, together with the detailed description, serve to explain the principles and implementations of the disclosure.

DETAILED DESCRIPTION

As used herein and in the appended claims, the singular forms “a,” “an,” and “the” include plural referents unless the context clearly dictates otherwise. Thus, for example, reference to “a flow cell” includes a plurality of such flow cells and reference to “the DNA library” includes reference to one or more DNA libraries, and so forth.

Also, the use of “or” means “and/or” unless stated otherwise. Similarly, “comprise,” “comprises,” “comprising,” “include,” “includes,” “including,” “have,” “haves,” and “having” are interchangeable and not intended to be limiting.

It is to be further understood that where descriptions of various embodiments use the term “comprising,” those skilled in the art would understand that in some specific instances, an embodiment can be alternatively described using language “consisting essentially of” or “consisting of.”

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The term “amplifying” or “amplification” herein is intended to mean the process of increasing the number of a template polynucleotide sequence by producing copies of the template. The amplification process can be either exponential or linear, but is typically exponential. In exponential amplification, the number of copies made of the template polynucleotide sequence increases at an exponential rate. For example, in an ideal amplification reaction of 30 rounds, one copy of template DNA will yield $2^{30}$ or 1,073,741,824 copies. However, bridging amplification as described herein does not typically occur under ideal conditions, and a 30-cycle “exponential” reaction may only yield a few hundred to a few thousand copies of the original template, mainly due to the limited localized concentration of surface bound primers and the competition with template re-hybridization. In linear amplification the number of copies made of the template polynucleotide sequences increases at a linear rate. For example, in an ideal 4-hour linear amplification reaction with a copying rate of 2000 copies per minute, each copy of template DNA will yield 480,000 copies.

The terms "denature" and "denaturation" are broad terms which refer primarily to the physical separation of the DNA bases that interact within for example, a Watson-Crick DNA-duplex of the single stranded polynucleotide sequence and its complement. The terms also refer to the physical separation of both of these strands. In their broadest sense the terms refer to the process of creating a situation wherein annealing of another primer oligonucleotide or polynucleotide sequence to one or both of the strands of a duplex becomes possible.

As used herein, the term "flow cell" is intended to mean a chamber having a surface across which one or more fluid reagents can be flowed. Generally, a flow cell will have at least one ingress opening and at least one egress opening to facilitate flow of fluid. Examples of flow cells and related fluidic systems and detection platforms that can be readily used in the methods of the disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, flow cells may house arrays. Arrays used for nucleic acid sequencing often have random spatial patterns of nucleic acid features. For example, HiSeq™ or MiSeg™ sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Exemplary patterned arrays, methods for their manufacture and methods for their use are set forth in U.S. patent application Ser. No. 13/787,396; U.S. patent application Ser. No. 13/783,043; U.S. patent application Ser. No. 13/784,368; U.S. Pat. App. Pub. No. 2013/0116153 A1; and U.S. Pat. App. Pub. No. 2012/0316086 A1, each of which is incorporated herein by reference. The features of such patterned arrays can be used to capture a single nucleic acid template molecule to seed subsequent formation of a homogenous colony, for example, via bridge amplification. Such patterned arrays are particularly useful for nucleic acid sequencing applications.

The term "isothermal" as used herein refers to processes in which the temperature of a system or device remains constant, i.e., wherein $\Delta T=0$. This optionally occurs when a system/device is in contact with an outside thermal reservoir (for example, a heater, a heat bath, thermoelectric controller (TEC), or the like), and actions or changes occur within the system/device at a rate that allows the system/device to continually adjust to the temperature of the reservoir through heat exchange.

As used herein, the terms "polynucleotide" or "nucleic acid" refers to deoxyribonucleic acid (DNA), however where appropriate, the skilled artisan will recognize that the systems and devices herein can also be utilized with ribonucleic acid (RNA). The terms should be understood to include, as equivalents, analogs of either DNA or RNA made from nucleotide analogs. The terms as used herein also encompass cDNA, that is complementary-, or copy-DNA produced from an RNA template, for example by the action of reverse transcriptase.

"Primer oligonucleotides" or "primers" are oligonucleotide sequences that are capable of annealing specifically to single stranded polynucleotide sequences to be amplified under conditions encountered in the primer annealing step of each cycle of an isothermal amplification reaction. Generally, amplification reactions require at least two amplification primers, often denoted "forward" and "reverse" primers. In certain embodiments the forward and reverse primers can be identical. The primer oligonucleotides can include a "template-specific portion," being a sequence of nucleotides capable of annealing to a primer-binding sequence in the single stranded polynucleotide molecule to be amplified (or the complement thereof when the template is viewed as a single strand) during the annealing step. The primer binding sequences generally will be of known sequences and will therefore particularly be complementary to a sequence within known sequence-1 and known sequence-2 of the single stranded polynucleotide molecule. The length of the primer binding sequences need not be the same as those of known sequence-1 or -2, and can be shorter, e.g., 16-50 nucleotides, 16-40 nucleotides, or 20-30 nucleotides in length. The optimum length of the primer oligonucleotides will depend upon a number of factors and it is common that the primers are long (complex) enough so that the likelihood of annealing to sequences other than the primer binding sequence is very low. In certain embodiments, the "primer oligonucleotides" are bound to the surface of a flow cell in a random manner (non-patterned flow cell) or bound to specific areas of flow cells, such as to the surfaces of wells (patterned flow cells). In further embodiments, the primers bound to the flow cells include P5 and/or P7 primers having the following sequences:

```
P5:
                                  (SEQ ID NO: 1)
5' AATGATACGGCGACCACCGA 3'

P7:
                                  (SEQ ID NO: 2)
5' CAAGCAGAAGACGGCATACGAGAT 3'
```

The polynucleotide molecules to be amplified are typically in single-stranded form, as ssDNA or RNA, or double-stranded DNA (dsDNA) form (e.g., genomic DNA fragments, PCR and amplification products and the like). Thus, a single stranded polynucleotide may be the sense or antisense strand of a polynucleotide duplex. Methods of preparation of single stranded polynucleotide molecules suitable for use in the systems/devices of the disclosure using standard techniques are known in the art. For example, single stranded polynucleotides from a complex mixture of polynucleotides can be generated by heating or treatment with hydroxide followed by dilution. The precise sequence of the primary polynucleotide molecules is generally not material to the disclosure, and may be known or unknown. The single stranded polynucleotide molecules can represent genomic DNA molecules (e.g., human genomic DNA) including both intron and exon sequence (coding sequence), as well as non-coding regulatory sequences such as promoter and enhancer sequences. In a particular embodiment, the polynucleotide molecules to be amplified comprise a DNA library. In a further embodiment, the DNA library is generated using a library preparation kit. In yet a further embodiment, the library preparation kit is from Illumina, Inc. (e.g., AmpliSeg™ kits, COVIDSeg™ kit, Illumina DNA prep kits, Illumina RNA prep kits, Nextera™ Kits, SureCell WTA™ Kits, TruSeq™ kits, and TruSight™ kits).

"Solid-phase amplification" as used herein refers to nucleic acid amplification reactions carried out on the surface of a channel of a flow cell so that all or a portion of the amplified products are immobilized on the solid support as they are formed.

During use of the system/devices described herein to amplify nucleic acids, primers for solid phase amplification are immobilized by covalent attachment to the solid support of the flow cell at or near the 5' end of the primer, leaving the template-specific portion of the primer free for annealing to its cognate template and the 3' hydroxyl group free for primer extension. The chosen attachment chemistry will depend on the nature of the solid support, and any functionalization or derivatization applied to it. The primer itself may include a moiety, which may be a non-nucleotide chemical modification to facilitate attachment. The primer can include a sulfur containing nucleophile such as phosphorothioate or thiophosphate at the 5' end. In the case of solid supported polyacrylamide hydrogels, this nucleophile can bind to a bromoacetamide group present in the hydrogel. For example, the primers can be attached to the solid support via 5' thiophosphate attachment to a hydrogel comprised of polymerized acrylamide and N-(5-bromoacetamidylpentyl) acrylamide (BRAPA).

Briefly, for isothermal amplifications, double stranded "adapter" sequences are ligated to each end of DNA segments (e.g., randomly fragmented genomic double stranded DNA) that are to be amplified. The DNA-adapter molecules are then flowed into a flow cell where they randomly attach to the surface of the flow cell channels to form an array of single molecules. If the ligated adaptor sequences contain moieties for surface attachment, then the DNA-adaptor sequences can be attached directly to the surface. In such case, the attachment is generally performed with an excess of primers complementary to at least a portion of one of the adaptor sequences at each end of the ligated segment. The array will therefore be a lawn of primers suitable for polymerase extension, with a dispersion of discreet single molecules suitable for amplification. If desired, the primer attachment can be performed after the formation of the disperse array of single molecules for amplification. The DNA-adaptor molecules can be attached either in single or double stranded form, provided that the double stranded form can be treated to give a free single stranded molecule suitable for amplification.

In an alternative embodiment a surface bound lawn of primers is prepared on a flow cell surface for use in the system/device of the disclosure, followed by hybridization of the DNA-adaptor sequences to the surface immobilized primers, to form a single molecule array of hybridized DNA-adaptors. If the lawn of primers is randomly located on the surface of the flow cell then the flow cell is a "non-patterned flow cell". If the lawn of primers is organized into an array of wells or similar structures that are separated from each other (where no primers are bound in these interstitial areas), then the flow cell is a "patterned flow cell." A cycle of extension with a polymerase and dNTPs to copy the hybridized strand, followed by denaturing of the original DNA-adaptor sequence produces the desired array of attached single DNA molecules in a single stranded form that can then be subjected to cycles of isothermal amplification. The surface of the flow cell thus comprises a lawn of single stranded primer sequences, allowing "bridge amplification" to occur. In bridge amplification, when the surface is exposed to conditions suitable for hybridization, the single stranded nucleic acid molecules to be amplified form a bridge so that the adapter sequence on their free end hybridizes with its complementary single stranded primer sequence bound to the surface of the flow cell. Nucleotides and DNA polymerase are then transported into the flow cell to create the complementary strand of the nucleic acid to be amplified. The double stranded sequences created are then denatured by flowing in a denaturing reagent, and the process starts again, thus creating clusters of amplified nucleic acid without changing the temperature of the system during the amplification cycles. In typical embodiments, the majority of the clusters are monoclonal, resulting from the amplification of a single original nucleic acid sequence.

Generally, primer oligonucleotides used to create DNA clusters are single stranded polynucleotides. They may also contain a mixture of natural and non-natural bases as well as natural and non-natural backbone linkages, provided that any non-natural modifications do not preclude function as a primer (i.e., the ability to anneal to a template polynucleotide strand during conditions of the amplification reaction and to act as an initiation point for synthesis of a new polynucleotide strand complementary to the template strand). One of the primers may contain a modification allowing the primer to be removed (cleaved) from the surface to allow the formation of single stranded clusters. Such linearized clusters can undergo hybridization with a further primer strand to allow a sequencing reaction to occur.

The polynucleotides to be amplified are immobilized in appropriate proportions so that when they are attached to the solid support of the flow cell an appropriate density of attached single stranded polynucleotide molecules and primer oligonucleotides is obtained ("polynucleotide seeding"). In the case of directly immobilized DNA-adaptor sequences, the proportion of primer oligonucleotides in the solution mixture used for the immobilization reaction is higher than the proportion of single stranded polynucleotide molecules. The immobilization reaction can then give a lawn of primers, with discreet single molecules of DNA-adaptor sequences. For the hybridized DNA-adaptor reactions, the density of clusters is controlled by the concentration of the DNA-adaptor sequences used to hybridize to the lawn of primers. The ratio of primer oligonucleotides to single stranded polynucleotide molecules is typically such that when immobilized to the solid support a "lawn" of primer oligonucleotides is formed, comprising a plurality of primer oligonucleotides being located at an approximately uniform density over the whole or a defined area of the flow cell channel with one or more single stranded polynucleotide molecules being immobilized individually at intervals within the lawn of primer oligonucleotides.

The distance between the individual primer oligonucleotides and the single stranded polynucleotide molecules (and hence the density of the primer oligonucleotides and single stranded polynucleotide molecules) can be controlled by altering the concentration of primer oligonucleotides and single stranded polynucleotide molecules that are immobilized to the flow cell surface.

A well-controlled polynucleotide seeding process can ensure the consistency of cluster density and sequencing quality. All types of sequencing flow cells have different channel geometric dimensions, surface primer density, patterned material and bonding methods, and all these factors affect how efficient the polynucleotides (e.g., DNA library) can be seeded onto the surface. It is important to understand and optimize polynucleotide seeding process, especially when the polynucleotide input is limited or when linked long reads are required. The seeding efficiency should be as close to 100% as possible.

Once the primer oligonucleotides and single stranded polynucleotides have been seeded and immobilized on the solid support at the appropriate density, extension products can then be generated by carrying out cycles of isothermal amplification on the covalently bound single stranded polynucleotide molecules so that each colony comprises multiple copies of the original immobilized single stranded polynucleotide molecule (and its complementary sequence). One cycle of amplification consists of the steps of hybridization, extension and denaturation. Such steps are generally comparable in terms of reagent components (e.g., buffers, etc.) with traditional nucleic acid amplification procedures such as PCR. Suitable reagents for amplifying nucleic acids (e.g., hybridization, extension, etc.) are well known in the art. Exemplary reagents are described in more detail below.

Thus a neutralizing/hybridizing buffer can be applied to the single stranded polynucleotide molecules and the plurality of primer oligonucleotides such that the unbound end of a surface bound single stranded polynucleotide molecule hybridizes to a surface bound primer oligonucleotide to form a complex (wherein the primer oligonucleotide hybridizes to and is complementary to a region or template specific portion of the single stranded polynucleotide molecule). This process creates a "bridge" structure. Again, see WO/0246456, U.S. Ser. No. 60/783,618, WO/9844151, and WO/0018957 for further discussion on bridge amplification.

Suitable neutralizing/hybridizing buffers are well known in the art (See Sambrook et al., Molecular Cloning, A Laboratory Manual, 3rd Ed, Cold Spring Harbor Laboratory Press, NY; Current Protocols, eds. Ausubel et al.) as well as the illustration section describing amplification below. Suitable buffers may comprise additives such as betaine or organic solvents to normalize the melting temperate of the different template sequences, and detergents. An exemplary hybridization buffer comprises 2 M betaine, 20 mM Tris, 10 mM Ammonium Sulfate, 2 mM Magnesium sulfate, 0.1% Triton, 1.3% DMSO, pH 8.8.

Next, an extension reaction is done by applying an extension solution comprising an enzyme with polymerase activity and dNTPs to the bridge complexes. The primer oligonucleotide of the complex is extended by sequential addition of nucleotides to generate an extension product complimentary to the single stranded polynucleotide molecule. Suitable extension buffers/solutions are well known in the art (See, e.g., Sambrook et al., Molecular Cloning, A Laboratory Manual, 3rd Ed, Cold Spring Harbor Laboratory Press, NY; Current Protocols, eds. Ausubel et al.) and examples below.

Examples of enzymes with polymerase activity that can be used in the systems/devices of the disclosure include DNA polymerase (Klenow fragment, T4 DNA polymerase) and heat-stable DNA polymerases from a variety of thermostable bacteria (such as Taq, VENT, Pfu, Bst and Tfl DNA polymerases) as well as their genetically modified derivatives (TaqGold, VENT exo, Pfu exo, etc.). It will be appreciated that since the amplification reactions performed on the flow cells are isothermal, that additional and/or alternative DNA polymerases can be used as compared to the polymerases for thermal cycling amplification, and, in most embodiments, there is no particular requirement for the polymerase to be thermostable. Also, while enzymes with strand displacing activity such as Bst polymerase show excellent performance in growing effective clusters for sequencing, any DNA polymerase can be used.

The nucleoside triphosphate molecules used to create DNA clusters are typically deoxyribonucleotide triphosphates, for example dATP, dTTP, dCTP, dGTP. The nucleoside triphosphate molecules may be naturally or non-naturally occurring.

After the hybridization and extension steps, the support and attached nucleic acids are subjected to denaturation conditions. Suitable denaturing buffers are well known in the art (See, e.g., Sambrook et al., Molecular Cloning, A Laboratory Manual, $3^{rd}$ Ed, Cold Spring Harbor Laboratory Press, NY; Current Protocols, eds. Ausubel et al.). The systems/devices of the disclosure produce isothermal nucleic acid amplification; therefore, the nucleic acid strands herein are not denatured through temperature elevation or manipulation, but rather by other methods (e.g., chemical, physical, etc.). By way of example it is known that alterations in pH and low ionic strength solutions can denature nucleic acids at substantially isothermal temperatures. Formamide and urea form new hydrogen bonds with the bases of nucleic acids disrupting hydrogen bonds that lead to Watson-Crick base pairing. These result in single stranded nucleic acid molecules. Alternatively, the strands can be separated by treatment with a solution of low salt and high pH (>12) or by using a chaotropic salt (e.g., guanidinium hydrochloride). In a particular embodiment, sodium hydroxide (NaOH) solution is used at a concentration of from about 0.25M to about 0.1 M. In an alternate embodiment 95% formamide in water, or 100% formamide is used. Such formamide embodiments show additional advantages as the hydroxide treatment can damage the surface and give clusters of lower intensity in some instances. As with the other reagents used, such denaturing reagents are passed through the flow channels.

Following denaturation, two immobilized nucleic acids will be present, the first being the initial immobilized single stranded polynucleotide molecule and the second being its complement, extending from one of the immobilized primer oligonucleotides. Both the original immobilized single stranded polynucleotide molecule and the immobilized extended primer oligonucleotide (the complement) formed are then able to initiate further rounds of amplification by subjecting the support to further cycles of hybridization, extension and denaturation. Such further rounds of amplification will result in a nucleic acid colony or "cluster" comprising multiple immobilized copies of the single stranded polynucleotide sequence and its complementary sequence. The initial immobilization of the single stranded polynucleotide molecule means that the single stranded polynucleotide molecule can only hybridize with primer oligonucleotides located at a distance within the total length of the single stranded polynucleotide molecule. Thus, the boundary of the nucleic acid colony or cluster formed is limited to a relatively local area in which the initial single stranded polynucleotide molecule was immobilized. The terms "cluster" and "colony" are used interchangeably herein to refer to a discrete site on a solid support comprised of a plurality of identical immobilized nucleic acid strands and a plurality of identical immobilized complementary nucleic acid strands. The term "clustered array" or "cluster array" refers to an array formed from such clusters or colonies. In this context the term "array" is not to be understood as requiring an ordered arrangement of clusters.

In typical embodiments, the nucleic acid to be amplified is immobilized upon the surface of a channel within a flow cell. The term "immobilized" as used herein is intended to encompass direct or indirect, covalent or non-covalent attachment, unless indicated otherwise, either explicitly or by context. In certain embodiments of the disclosure, covalent attachment is typical, but generally all that is required is that the molecules (e.g., nucleic acids) remain immobilized or attached to the support under conditions in which it is intended to use the support, for example in applications for amplification. The immobilized nucleic acid molecule for amplification can be obtained either by direct attachment of a suitably modified nucleic acid molecule (either single or double stranded) to a suitably reactive surface, or by hybridization to a surface immobilized primer, followed by a cycle of extension with a polymerase and dNTPs to copy the hybridized strand. The extended strand, or the chemically attached duplex, can then be subject to denaturing conditions to produce the desired immobilized, single stranded nucleic acid molecule that can then be subjected to cycles of isothermal amplification by the instrumentation described herein. The initial step of hybridizing the DNA from solution onto the flow cell can be performed at a higher temperature than the subsequent amplification reactions, which then take place at a substantially isothermal temperature. The hybridization step may also be carried out at the amplification temperature, provided the input nucleic acids strands are supplied to the surface in a single stranded form.

Some embodiments of preparing a template nucleic acid can include fragmenting a target nucleic acid. In some embodiments, barcoded or indexed adapters are attached to the fragmented target nucleic acid (e.g., DNA library). Adapters can be attached using any number of methods known in the art such as ligation (enzymatic or chemical), tagmentation, polymerase extension, and so forth. In some embodiments, insertion of transposomes comprising non-contiguous transposon sequences can result in fragmentation of a target nucleic acid. In some embodiments comprising looped transposomes, a target nucleic acid comprising transposon sequences can be fragmented at the fragmentation sites of the transposon sequences. Further examples of method useful to fragment target nucleic acids useful with the embodiments provided herein can be found in for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

Various flow cell devices can be used to carry out the methods of the disclosure, including flow cell devices made by Illumina, Inc. (e.g., HiSeq devices, NovaSeq devices, MiSeq devices, and NextSeq devices); flow cell devices made by F. Hoffmann-La Roche Ltd. (e.g., GS FLX devices, and GS Junior devices); and flow cell devices made by Life Sciences (e.g., SOLiD/Ion Torrent devices). In a particular embodiment, the flow cell device used to carry out a method of the disclosure is a flow cell device made by Illumina Inc.

A flow cell typically comprises 1 or more fluidic channels. In a further embodiment, 1, 2, 3, 4, 5, 6, 7, 8 or more fluidic channels of a flow cell can be evaluated for polynucleotide seeding efficiency using a method disclosed herein. As already indicated herein primers can be bound or immobilized to the surface of flow cells. Typically, the primers bound to the flow cell are single stranded DNA containing primers containing known sequences. In order to perform bridge PCR amplification, it is beneficial to have multiple populations (e.g., 2, 3, 4, etc.) of primers with different but known sequences. For example, Illumina flow cells comprise P5 (SEQ ID NO:1) and P7 (SEQ ID NO:2) primers bound to the surface of the flow cells to allow for bridge amplification of target polynucleotides. These target polynucleotides are bridge amplified by comprising adaptor sequence at the terminal ends of the polynucleotides which have complementary sequences to the P5 and P7 primers. Such adaptors can be added to the ends of polynucleotides using reduced copy PCR with primers which contain said sequences. These primers can further comprise barcode or index sequences. The primers can be attached to the surface of a flow cell by using standard chemistries, including silane chemistries, or by attachment to polymers deposited on the flow cell surface (e.g., see US Pat. Pub. No. US20120316086A1, and PCT Pub. No. WO2017201198A1). The primers can be attached or immobilized on the surface of the flow cell in a random fashion or as an organized array (i.e., patterned flow cell). For examples, the flow cell surface can comprise and ordered array of micro or nano wells that contain bound immobilized primers. The polynucleotides used to seed a flow cell described herein can come from any source, including from various organism from the different phylogenetic kingdoms. For example, the polynucleotides can be fragmented genomic DNA that has been isolated from a human subject. In a particular embodiment, the polynucleotides are in the form of a DNA library. The process to make DNA libraries from source genomic DNA are known in the art and many library preparation kits are commercially available. In a particular embodiment, the library preparation kit is from Illumina, Inc (e.g., AmpliSeq™ kits, COVIDSeq™ kit, Illumina DNA prep kits, Illumina RNA prep kits, Nextera™ Kits, SureCell WTA™ Kits, TruSeq™ kits, and TruSight™ kits). The steps of the library preparation kit can include the following: (A) simultaneous fragmenting and adding primers to isolated DNA using transposomes; (B) amplifying the fragmented DNA using reduced-cycle PCR, wherein the PCR amplification primers comprise index and adapter sequences; and (C) washing and pooling the amplified DNA fragments to form a DNA library. The transposomes can be bound to a sold substrate, like beads. The polynucleotides can be seeded in the flow cell for a defined length of time including for 10 sec, 20 sec, 30 sec, 40 sec, 50 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 60 min, 90 min, 120 min, or a range that includes or is in between any two of the foregoing time points (e.g., 5 min to 60 min, 10 min to 40 min, etc.), including fractional increments thereof.

Usually, the investigation of polynucleotide seeding efficiency (e.g., DNA library seeding efficiency) is done by looking at how many polynucleotides are captured by counting the final cluster numbers. The disclosure provide methods of determining seeding efficiency.

This disclosure provides in one embodiment a method for determining polynucleotide seeding efficiency by looking at the polynucleotides that are not captured on the surface and remain in the bulk seeding solution. By collecting and analyzing the supernatant from the flow cell channel at the end of seeding process, more detailed information regarding the seeding process can be determined. The methods disclosed herein are useful for checking the seeding on patterned flow cells, in which the cluster number does not directly correlate to number of polynucleotide seeded due to, for example, (1) poly-clonality, (2) ex-amplification duplicates, and (3) library adsorption at interstitial areas between wells (see FIG. 1).

In a particular embodiment, the disclosure provides a method to evaluate the seeding efficiency of a flow cell with polynucleotides, comprising: seeding a flow cell with polynucleotides for at least 1 minute and collecting the supernatant; quantifying the polynucleotides in the supernatant by using step (a) or (b): (a) amplifying the polynucleotides in the supernatant using qPCR and/or droplet PCR; or (b) reseeding the supernatant using a second flow cell and counting clusters generated after bridge amplification of the polynucleotides; and determining seeding efficiency of the flow cell by comparing the number of polynucleotides quantified in the supernatant vs. the number of polynucleotides used to seed the flow cell.

The supernatant is recovered after the seeding process and the polynucleotides are quantified using a method disclosed herein, including the use of qPCR or droplet PCR, or by seeding another flow cell. A real-time polymerase chain reaction (real-time PCR), also known as quantitative polymerase chain reaction (qPCR), is a laboratory technique of molecular biology based on the polymerase chain reaction (PCR). It monitors the amplification of a targeted DNA molecule during the PCR (i.e., in real time), not at its end, as in conventional PCR. Real-time PCR can be used quantitatively (quantitative real-time PCR) and semi-quantitatively (i.e., above/below a certain amount of DNA molecules) (semi-quantitative real-time PCR). Two common methods for the detection of PCR products in real-time PCR are (1) non-specific fluorescent dyes that intercalate with any double-stranded DNA and (2) sequence-specific DNA probes consisting of oligonucleotides that are labelled with a fluorescent reporter, which permits detection only after hybridization of the probe with its complementary sequence. The qPCR reaction described herein can utilize any commercially available thermally stable polymerase used for such PCR reactions and can use either the double stranding binding dye for quantification or the use of probe/quencher system. Examples of double stranded binding dyes include, but are not limited to, SYBR® Green I, BRYT Green® Dye, PicoGreen, YOYO-1 iodide, and SYBR® Gold. In a particular embodiment, the qPCR reaction disclosed herein utilizes a sequence specific probe that is labeled with a fluorescent reporter and a quencher molecule that binds to a DNA template. Typically, quencher molecule is a dark quencher that absorbs light over multiple wavelengths and does not emit light. Examples of dark quencher include, but are not limited to, Dabsyl, Black Hole Quenchers, Iowa Black FQ, Iowa Black RQ, IRDye QC-1, and Qxl quenchers.

In an alternate embodiment, the disclosure provides that the polynucleotides in the supernatant are quantified by counting clusters generated from seeding another flow cell with the supernatant. For example, supernatant obtained from seeding a HiSeq or NextSeq flow cell (up to 120 Gb of sequence data) can be used with a MiSeq flow cell (up to 12 Gb of sequence data) for quantification. Other permutations/ combination with commercially available flow cells are also envisaged using such a process.

Figure 6A:
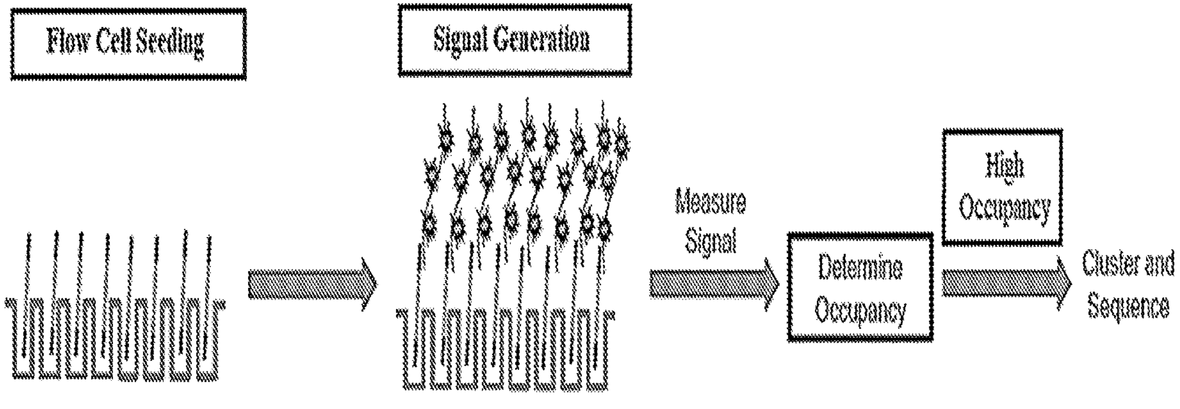
FIG. 6A-B shows a method of the disclosure for determining flow cell seeding using label capture or assembly. (A) Shows a process where high flow cell seeding occupancy occurs followed by cluster and sequencing. (B) Shows a process whereby low flow cell seeding occupancy is determined followed by further seeding repetition to a desired seeding occupancy.

The disclosure also provides a method of quantifying flow cell seeding via Library-Mediated Fluorophore Capture or Assembly (LMFCA). In an LMFCA method of the disclosure, seeding efficiency is measure in the flow cells using detectable labels. For example, the disclosure provides a method to evaluate the seeding efficiency of a flow cell with polynucleotides, comprising: seeding a flow cell with polynucleotides for at least 1 minute; labeling the bound/seeded polynucleotides in the flow cell with a detectable; quantifying the labelled polynucleotides in the flow cell and, depending upon the seeding efficiency, removing the label and reseeding the flow cell (see, e.g., FIG. 6B) or removing the label and proceeding to cluster and/or sequence (see, e.g., FIG. 6*h*).

Methods of labeling nucleotides on flow cells include, but are not limited to, (i) the use of labeled nucleotides and polymerases; (ii) the use of DNA dendrimers or labeled nanoparticles having fluorophore labels and a complementary oligo for hybridization to seeded polynucleotides; (iii) growing labeled structure from the seeded polynucleotides; and (iv) labeled adapters that bind to seeded polynucleotides (see FIG. 7).

Suitable labels include fluorescent labels, luminescent labels, radioactive labels, chromogenic labels and the like. Typically, the label will be fluorescent or luminescent such that it can be detected and quantitated using a CCD camera or the like.

Figure 6B:
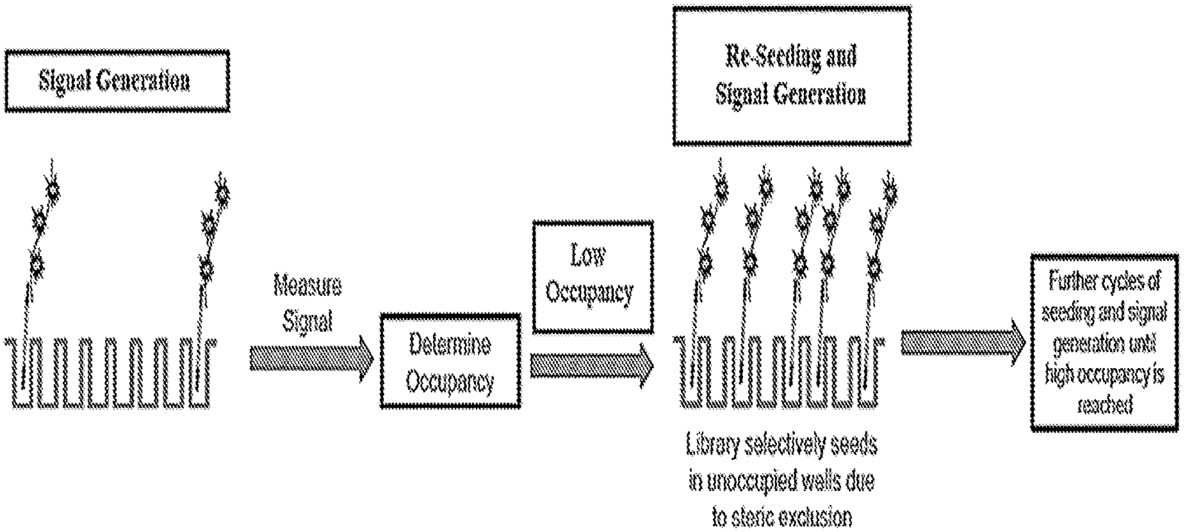
Figure 7:
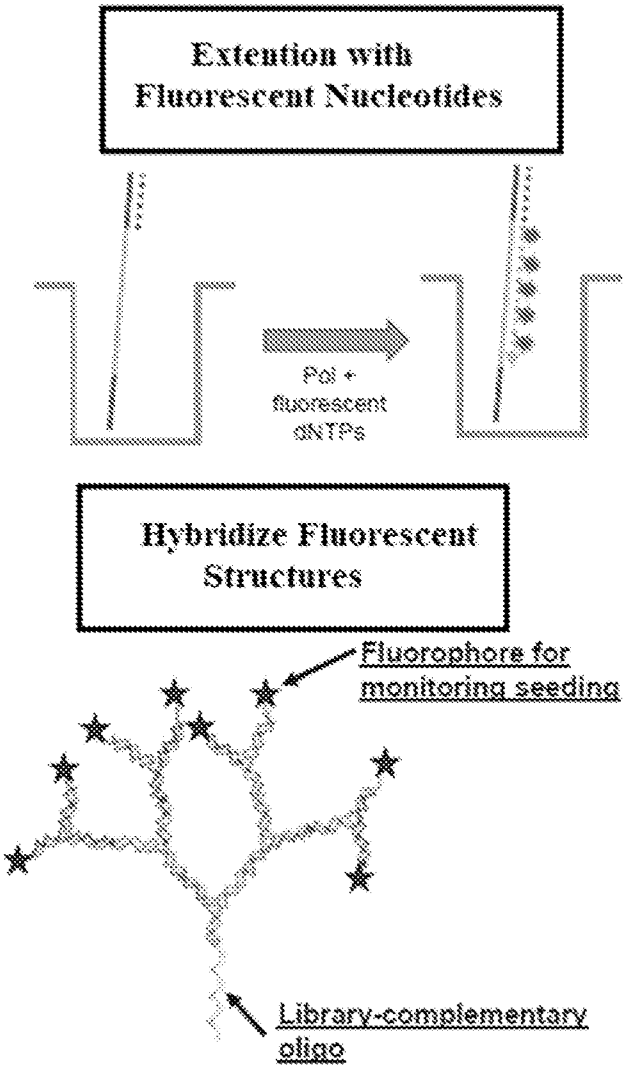
FIG. 7 shows various signal generation strategies that can be used in the methods of the disclosure (see, e.g., FIGS. 6A-B).
Figure 7:
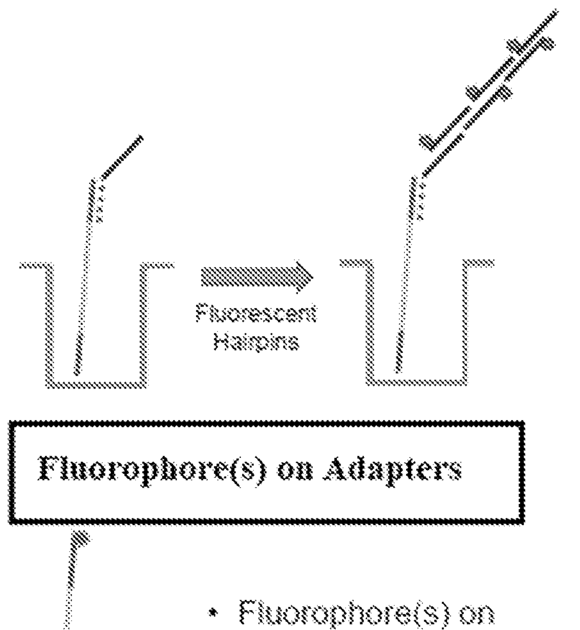

In one embodiment, a flow cell is seeded with composition comprising polynucleotides that comprise at least one adaptor region under conditions and for a desired time suitable to allow the polynucleotides to "seed" the flow cell. The polynucleotides can be seeded in the flow cell for a defined length of time including for 10 sec, 20 sec, 30 sec, 40 sec, 50 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 60 min, 90 min, 120 min, or a range that includes or is in between any two of the foregoing time points (e.g., 5 min to 60 min, 10 min to 40 min, etc.), including fractional increments thereof. As shows in FIG. 6, once the flow cell undergoes an initial seeding, the flow cell is contact with a composition that labels polynucleotides that have been seeded and retained on the flow cell. Typically, the flow cell will be washed to remove any unbound polynucleotides prior to contacting with the composition that labels the polynucleotides seeded on the flow cell. As depicted in FIG. 7, various techniques to label polynucleotide bound to the flow cell are depicted. The flow cell is then imaged or select regions of the flow cell are imaged to determine the amount of label or "signal" (e.g., fluorescence) present in order to determine the efficiency of seeding. The "signal" is typically compared to a known signal comprising a particular seeding efficiency in order to determine the seeding efficiency of the experimental measurement. As shows in FIG. 6A, if there is sufficient seeding based upon the measured signal that can be indicative of a particular occupancy of the flow cell or a site on the flow cell. If the occupancy of the flow cell is at the desired amount that flow cells is then processed to induce clustering and/or for sequence analysis. As depicted in FIG. 6B, if the seeding efficiency is too low or inadequate based upon the measure signal, then the collected unbound polynucleotide obtained from the initial seeding, can be used to 're-seed' the flow cells and the signal measurements performed again to determine seeding efficiency. This process can be repeated until there is a desired seeding on the flow cell in order to perform clustering and/or sequencing.

As depicted in FIG. 7, incorporation of labeled (e.g., fluorescently labeled) nucleotides to label a seeded polynucleotide can be performed using an adapter sufficient to allow binding of a polymerase under conditions to extend a complementary strand of the seeded polynucleotide in the presence of the labeled nucleotides. The labeled complementary strand is not de-hybridized until after quantifying the amount of signal in the flow cell. Once the quantitation of the signal is complete the labeled complementary nucleic acid can be remove by heat and/or salt content.

In another embodiment of FIG. 7, a seeded polynucleotide in a flow cell may be labeled using a labeled structure that comprises a sequence complementary to, e.g., an adapter sequence on the seeded polynucleotide. The sequence complementary to the adapter sequence linked to the labeled structure will hybridize to the adapter sequence on the seeded polynucleotide and thus "link" the labeled structure to the seeded polynucleotide. The labeled structure can be a nanoparticle comprising a fluorescent moiety, or a dendrimer comprising one of more fluorescent moieties. The labeled structure is not removed until after quantifying the amount of signal in the flow cell. Once the quantitation of the signal is complete the labeled structure can be remove by, for example, cleaving off the adapter sequence and/or dehybridizing/denaturing the oligonucleotide hybridized to the adapter sequence.

In yet another embodiment of FIG. 7 there is depicted a method of labeling seeded polynucleotide comprising growing a labeled structure from the end of a seeded oligonucleotide. In this embodiment, an oligonucleotide or cognate to an adapter sequence on a seeded polynucleotide binds to the seeded polynucleotide and an oligonucleotide structure is grown from the adapter, wherein the structure is detectably labeled. The grown structure is not removed until after quantifying the amount of signal in the flow cell. Once the quantitation of the signal is complete the structure can be remove by, for example, cleaving off the adapter sequence and/or dehybridizing the oligonucleotide hybridized to the adapter sequence.

In yet another embodiment of FIG. 7, a labeled adapter can be attached to the seeded polynucleotide and then quantitated to determine the amount of label and thereby the amount of seeded polynucleotide in the flow cell. The labeled adapter can be cleaved or removed after first strand extension. The labeled adapter will comprise a sequence complementary to a cognate adapter nucleotide acid sequence on the polynucleotide or will comprise a cognate to a binding partner on the polynucleotide (e.g., biotin/streptavidin etc.). The adapter will comprise a detectable label such as a fluorescent label.

For use in flow cell applications described herein, kits and articles of manufacture are also provided. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more qPCR and/or MiSeq reagents described herein. The container(s) optionally have a sterile access port (for example the container can be a solution bag or a vial having a stopper pierceable by a hypodermic injection needle). Such kits optionally comprise reagents with an identifying description or label or instructions relating to its use in the methods described herein.

A kit will typically comprise one or more additional containers, each with one or more of various materials (such as additional reagents, optionally in concentrated form, and/or devices) desirable from a commercial and user standpoint for use of in the methods described herein. Non-limiting examples of such materials include, but are not limited to, buffers, diluents, filters, needles, syringes, carrier, package, container, vial and/or tube labels listing contents and/or instructions for use, and package inserts with instructions for use. A set of instructions will also typically be included.

An instruction label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific flow cell application. The label can also indicate directions for use of the contents, such as in the methods described herein.

EXAMPLES

Figure 2:
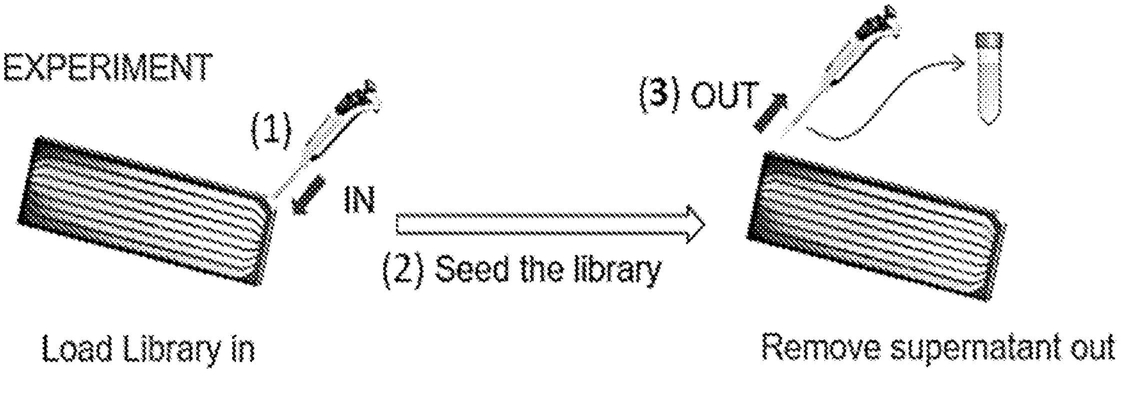
FIG. 2 provides an embodiment of an experimental workflow that comprises the steps: (1) loading a known concentration library to a flow cell, (2) seeding the library, and (3) removing the leftover supernatant for quantification.
Figure 3:
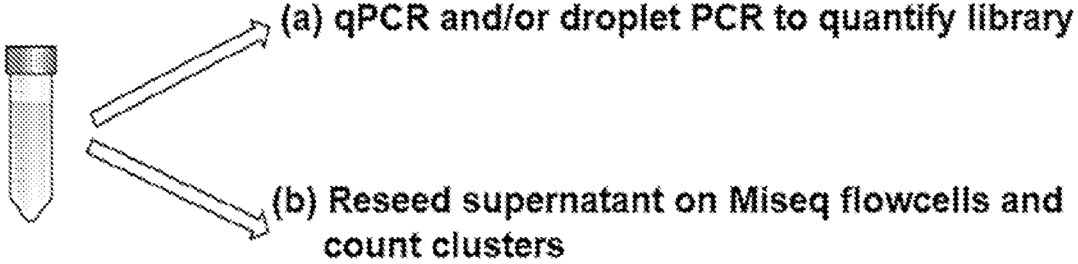
FIG. 3 diagrams two methods for quantifying library seeding efficiency: (a) qPCR or droplet PCR, and (b) reseeding supernatant on Miseq flow cells.

Overview for quantification of library seeding in a flow cell device. A flow cell was loaded with a known DNA library concentration (see FIG. 2). After library seeding, the supernatant was removed from the flow cell lanes, and the unseeded library fragments were quantified. Two methods were developed for quantifying the unseeded library fragments from the collected supernatant (see FIG. 3). One method uses qPCR or droplet PCR to determine the unseeded library concentration in supernatant, while the other method uses Illumina Miseq flow cells to determine sequencing cluster count results.

Figure 4A:
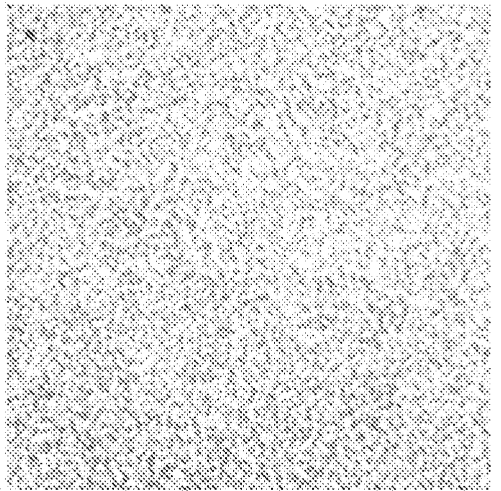
FIG. 4A-D shows the quantification results of library seeding using Miseq flow cells. (A)-(B) Shows the leftover library that is not getting seeded from pattern flow cell after 5 min seeding is much more than leftover from regular flow cell. (C)-(D) Pattern flow cell shows that with longer incubation during seeding can reduce the leftover library fragments that is not getting seeded.
Figure 4B:
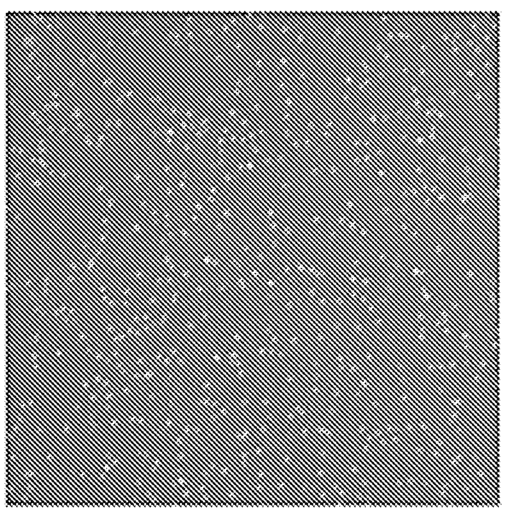
Figure 4C:
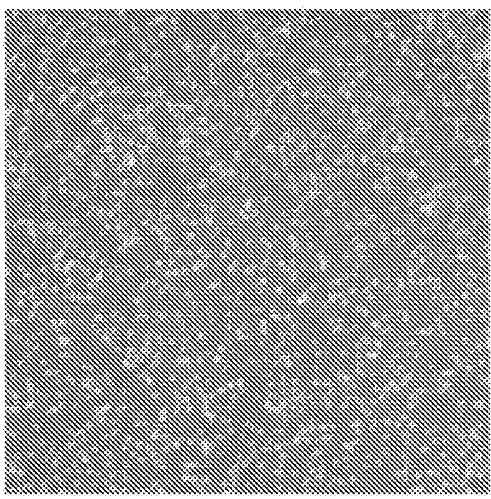
Figure 4D:
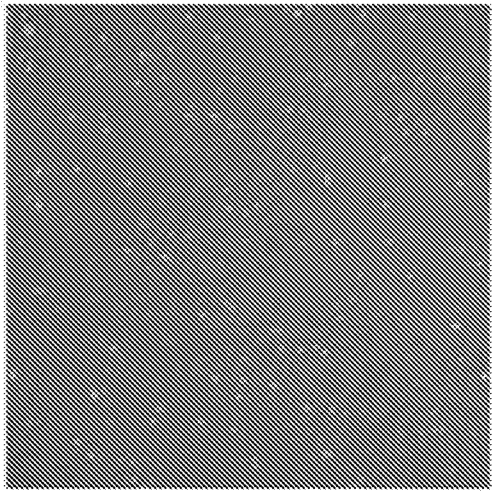

Quantification of library seeding supernatant using Miseq. The results of seeding supernatant collected from either patterned Hiseq FC or regular Hiseq FC with different seeding time are presented in the Miseq cluster images presented in FIG. 4. Within 5 min of seeding time, there was more DNA in the supernatant collected from the patterned Hiseq channel, implying less seeding efficiency in patterned Hiseq flow cell compared with regular non-patterned flow cell (see FIG. 4A-B). If the library seeding time is extended to 60 min, there is less DNA left in the supernatant, but there is still a population of DNA fragments that are not able to be captured onto the surface for clustering (see FIG. 4C). Accordingly, the effectiveness of the seeding process can be determined, including on a temporal basis. Moreover, the seeding efficiencies on patterned and non-patterned flow cells can also be compared which is not possible using current methods.

Figure 5:
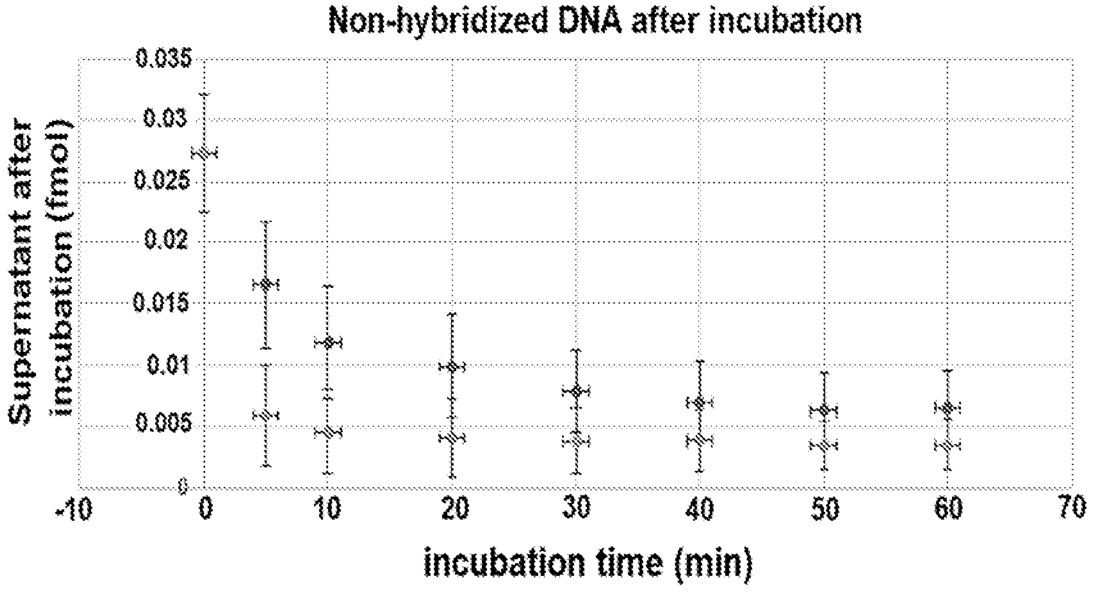
FIG. 5 demonstrates real-time seeding process in patterned FC (blue data set) and non-patterned FC (green data set) by supernatant analysis. Within 5 min of seeding time, the majority of DNA library are seeded in the case of non-patterned FC lane, results in very small amount of DNA left in supernatant (green); while in the case of patterned FC, ~50% of DNA library are un-seeded and stay in supernatant after 5 in (blue). This new tool helps us to monitor the seeding process in a time-lapsed fashion.

Quantification of library seeding supernatant using qPCR. Quantification of the seeding efficiency of the flow cells was also tested with qPCR. The patterned flow cell lanes and non-patterned flow cell lanes were seeded with the same concentration of a DNA library. After which, the supernatant from different lanes was collected at specific time points for analysis. The qPCR analysis demonstrates that seeded/non-seeded to a specific flow cell surface can be monitored in a time-lapsed fashion. Further, a DNA library takes longer to get captured by a p5/p7 surface on patterned flow cell than to the surface of a non-pattered flow cell (see FIG. 5). Using the foregoing technique, one can evaluate surface attractive force dynamics so as to engineer surfaces that provide for more efficient polynucleotide seeding on patterned flow cells.

A number of embodiments of the disclosure have been described. Nevertheless, it will be understood that various modifications may be made without departing from the spirit and scope of the disclosure. Accordingly, other embodiments are within the scope of the following claims.

The invention claimed is:

1. A method to evaluate the seeding efficiency of a flow cell with polynucleotides, comprising:

seeding a flow cell with a known concentration of polynucleotides for at least 1 minute, and collecting the supernatant; quantifying the polynucleotides in the supernatant by using step (a) or (b):

(a) amplifying the polynucleotides in the supernatant using qPCR and/or droplet PCR; or (b) reseeding the supernatant using a second flow cell and counting clusters generated after bridge amplification of the polynucleotides; and (c) determining seeding efficiency of the flow cell by comparing the number of polynucleotides quantified in the supernatant versus the number of polynucleotides used to seed the flow cell.

2. The method of claim 1, wherein one or more channels of a flow cell is evaluated for polynucleotide seeding efficiency.

3. The method of claim 1, wherein the flow cell comprises a plurality of primers bound to the surface of the flow cell.

4. The method of claim 3, wherein the bound primers comprise P5 primers which have the sequence of SEQ ID NO: 1 and/or are P7 primers which have the sequence of SEQ ID NO:2.

5. The method of claim 3, wherein the plurality of primers are randomly bound to the surface or bound to specific areas of the flow cell.

6. The method of claim 5, wherein the plurality of primers are bound to the surface of an array of wells that are patterned on the flow cell surface.

7. The method of claim 1, wherein the flow cell is used in a next generation sequencing device.

8. The method of claim 1, wherein the polynucleotides comprise adaptors.

9. The method of claim 8, wherein the adaptors are bridge PCR compatible.

10. The method of claim 1, wherein the polynucleotides comprise a DNA library.

11. The method of claim 10, wherein the DNA library is generated using a library preparation kit.

12. The method of claim 11, wherein the DNA library is prepared according to a method comprising the steps:

(A) simultaneous fragmenting and adding primers to isolated DNA using transposomes;

(B) amplifying the fragmented DNA using reduced-cycle PCR, wherein the PCR amplification primers comprise index and adapter sequences; and (C) washing and pooling the amplified DNA fragments to form a DNA library.

13. The method of claim 12, wherein the transposomes are linked to beads.

14. The method of claim 1, wherein the polynucleotides are seeded in the flow cell from 5 min to 60 min.

15. The method of claim 1, wherein the qPCR comprises a double stranded binding dye that allows for quantification of a double stranded amplified product based upon the level of fluorescence.

16. The method of claim 15, wherein the qPCR comprises a sequence specific probe that is labeled with a fluorescent reporter and a quencher molecule that binds to a DNA template.

17. The method of claim 16, wherein the quencher molecule is a dark quencher that absorbs light over multiple wavelengths.

18. The method of claim 1, wherein the second flow cell is used to quantitate the polynucleotides in the supernatant is different from the flow cell that is seeded with polynucleotides.

19. The method of claim 18, wherein the second flow cell provides up to 12 Gb of sequence data per run while the flow cell that is seeded with polynucleotides provides up to 120 Gb of sequence data per run.

20. The method of claim 1, wherein the method is performed multiple times using flow cells that were seeded with the same concentration of polynucleotides but with different seeding lengths of time.

21. The method of claim 20, wherein the seeding efficiency of a flow cell with polynucleotides is evaluated over various time points in time-lapse fashion.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: P5 primer

<400> SEQUENCE: 1
aatgatacgg cgaccaccga 20

<210> SEQ ID NO 2
<211> LENGTH: 24
<212> TYPE: DNA
<213> ORGANISM: Artificial Sequence
<220> FEATURE:
<223> OTHER INFORMATION: P7 primer

<400> SEQUENCE: 2
caagcagaag acggcatacg agat 24